US00PP21152P2

(12) United States Plant Patent
Klemm et al.

(10) Patent No.: US PP21,152 P2
(45) Date of Patent: Jul. 6, 2010

(54) ***NEMESIA* PLANT NAMED 'KLENH08448'**
(50) Latin Name: *Nemesia hybrida*
Varietal Denomination: KLENH08448

(75) Inventors: Nils Klemm, Stuttgart (DE); Katinka Wilde, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/384,084

(22) Filed: Mar. 31, 2009

(51) Int. Cl.
*A01H 5/00* (2006.01)

(52) U.S. Cl. ..... Plt./458
(58) Field of Classification Search ..... Plt./458
See application file for complete search history.

*Primary Examiner*—Kent L Bell
(74) *Attorney, Agent, or Firm*—Jondle & Associates, P.C.

(57) ABSTRACT

A new cultivar of *Nemesia* named 'KLENH08448' particularly characterized by purple veins on the lower surface of the petals, violet eyes on the upper lip of the petals, and petal lower lip includes a convex oval protuberance which serves as a pollinator nectar guide and landing platform, is disclosed.

1 Drawing Sheet

Genus and species: *Nemesia hybrida.*
Variety denomination: 'KLENH08448'.

BACKGROUND OF THE NEW PLANT

The present invention comprises a new and distinct cultivar of *Nemesia*, botanically known as *Nemesia hybrida*, and hereinafter referred to by the cultivar name 'KLENH08448'. 'KLENH08448' originated from an open pollination made in June 2005 in Stuttgart, Germany between the proprietary female *Nemesia* plant 'NH05279' (unpatented) and an unknown male *Nemesia* plant. A single plant selection was subsequently chosen for further evaluation and for asexual propagation.

The new cultivar was first propagated in September 2006 by vegetative cuttings in Stuttgart, Germany and has been asexually reproduced repeatedly by vegetative cuttings and in-vitro propagation in Stuttgart, Germany for about a two and one-half year period (about 6 generations). 'KLENH08448' has been found to retain its distinctive characteristics through successive asexual propagations.

SUMMARY OF THE INVENTION

The following are the most outstanding and distinguishing characteristics of this new cultivar when grown under normal commercial practices in a greenhouse in Stuttgart, Germany.

1. Purple veins on the lower surface of the petals;
2. Violet eyes on the upper lip of the petals; and
3. Petal lower lip includes a convex oval protuberance which serves as a pollinator nectar guide and landing platform.

DESCRIPTION OF THE PHOTOGRAPH

This new *Nemesia* plant is illustrated by the accompanying photograph which shows a close-up of the mature flowers, buds and foliage.

The colors shown are as true as can be reasonably obtained by conventional photographic procedures.

The photograph is of a plant about 14-weeks old and grown from rooted cuttings in 10.5 cm pots in a greenhouse (glasshouse) in Stuttgart, Germany in spring 2008 under conditions which approximate those generally used in commercial practice.

DESCRIPTION OF THE NEW CULTIVAR

The following detailed descriptions set forth the distinctive characteristics of 'KLENH08448'. The data which define these characteristics were collected from asexual reproductions carried out in Stuttgart, Germany. The plant history was taken on 14-week old plants in 10.5 cm pots that were pinched once after 10 weeks and grown in a greenhouse in spring 2008. The color readings were determined under natural light. Color references are to The R.H.S .Colour Chart of The Royal Horticultural Society of London (R.H.S.) (2001).

DESCRIPTION OF THE NEW PLANT

Classification:
- *Family.*—Scrophulariaceae.
- *Genus and species.*—*Nemesia hybrida.*
- *Common name.*—*Nemesia.*

Parentage:
- Female parent.—The proprietary female *Nemesia* plant 'NH05279' (unpatented).
- *Male parent.*—Unknown.

Plant:
- *Habit or form.*—Semi-trailing.
- *Vigor.*—Vigorous.
- *Height* (*measured from the top of the soil, including any flowers*).—24.0 cm.
- *Spread/width* (*horizontal plant diameter, including any flowers*).—About 35.0 cm.
- *Life cycle.*—Annual.
- *Time to produce a rooted cutting.*—About 3 weeks
- *Time to produce a finished flowering plant.*—About 10 weeks.
- *Flowering season.*—Spring.
- *Root description.*—Filiform, pale-colored roots with root hairs.
- *Rooting habit.*—High root density and freely branching.
- *Temperature tolerances.*—5° C. to about 35° C.
- *Environmental conditions for plant growth and performance.*—Tolerates wind and rain and has good outdoor performance.

Branches:
- *Type.*—Freely branching.
- *Quantity per plant.*—About 30.
- *Length.*—22.0 cm to 30.0 cm.

*Diameter.*—0.3 cm to 0.4 cm.
*Internode length.*—4.0 cm to 5.0 cm.
*Strength of branches.*—Fleshy, robust.
*Shape of branches in cross-section.*—Square.
*Color.*—RHS 143B for immature branches, fading to RHS 145A for mature branches.
*Texture.*—Smooth.
*Stem anthocyanin.*—Absent.
*Branch pubescence.*—Absent.

Leaves:
*Arrangement.*—Opposite and sessile.
*Shape.*—Lanceolate.
*Apex.*—Cuspidate.
*Base.*—Obtuse.
*Margin.*—Serrate.
*Length.*—3.5 cm to 6.0 cm.
*Width.*—0.5 cm to 2.5 cm.
*Color.*—Upper surface: RHS 143A for immature leaves and RHS 144A for mature leaves. Lower surface: RHS 143C for both immature and mature leaves.
*Variegation.*—Absent.
*Surface texture* (*both surfaces*).—Smooth.
*Venation pattern.*—Pinnate.
*Venation color.*—Upper surface: RHS 143A for immature and mature leaves. Lower surface: RHS 143C for immature and mature leaves.
*Petioles.*—Absent.

Flower bud:
*Quantity per inflorescence.*—2 to 6.
*Shape.*—Obovate.
*Surface texture.*—Smooth.
*Diameter.*—0.4 cm to 0.6 cm.
*Length.*—0.8 cm to 1.2 cm.
*Color* (*at tight bud*).—RHS 145D with RHS 61B venation.

Inflorescence:
*Inflorescence type.*—Raceme.
*Lastingness of inflorescence on the plant.*—About 7 days.
*Quantity of flowers per inflorescence.*—Up to 10.
*Inflorescence length.*—5.0 cm to 12.0 cm.
*Inflorescence diameter.*—About 3.0 cm not including the flowers and about 6.0 cm including the flowers.
*Flower diameter.*—About 2.0 cm.
*Flower depth* (*including nectar spur*).—1.2 cm.
*Nectar spur length.*—About 0.5 cm.
*Fragrance.*—Faint, typical of *Nemesia.*
*Self-cleaning or persistent.*—Self-cleaning.

Petals:
*Arrangement and shape.*—Zygomorphic; flowers are arranged on terminal racemes; four upper petals are fused at the base to form an upright lobed and arched banner lip and the fifth lower petal is modified into a large lip with convex oval protuberance which serves as a pollinator nectar guide and landing platform.
*Quantity per flower.*—5.
*Length* (*both the upper and lower lips*).—2.0 cm to 2.5 cm.
*Width.*—Upper lip: About 2.0 cm. Lower lip: About 1.7 cm.
*Apex.*—Lobate/abtuse.
*Margin.*—Entire.
*Color.*—Upper lip: Upper or forward facing surface: RHS 155B and color of eye is RHS 83A. Lower or rear facing surface: RHS 155B with veins of RHS 81A. Lower lip: Upper or forward facing surface: RHS 155B and color of nectar guides is RHS 12A. Lower or rear facing surface: RHS 155B and color of nectar guides is RHS 12A.
*Texture* (*both surfaces of upper and lower lips*).—Smooth, no pubescence.
*Nectar spur color.*—RHS 4D with RHS 61B venation.
*Nectar guide color.*—RHS 12A.
*Spur length.*—About 0.5 cm.
*Spur diameter at the base.*—About 0.4 cm.
*Spur diameter at the tip.*—About 0.1 cm.
*Spur texture.*—Smooth.

Calyx:
*Shape and arrangement.*—Star-shaped with 5 sepals fused at the base.
*Sepals.*—Quantity: 5. Apex: Cuspidate. Base: Fused. Margin: Entire. Color (both surfaces): RHS 139B. Length: 0.5 cm. Diameter: 0.6 cm. Surface texture (both surfaces): Pubescent.

Pedicel:
*Length.*—About 1.5 cm.
*Diameter.*—About 0.1 cm.
*Color.*—RHS 139B.
*Surface texture.*—Pubescent.

Peduncle:
*Length.*—About 5.0 cm.
*Diameter.*—About 0.2 cm.
*Color.*—RHS 143A.
*Surface texture.*—Pubescent.

Reproductive organs:
*Stamens.*—Number per flower: 4. Length: 0.3 cm. Filament color: RHS 155C. Filament length: 0.2 cm. Filament diameter: 0.05 cm. Anther color: RHS 20B. Anther length: 0.1 cm. Pollen amount: Moderate. Pollen color: RHS 20C.
*Pistil.*—Pistil number: 1. Pistil length: 0.3 cm. Stigma color: RHS 194D. Stigma length: Not distinguishable from style. Style length: 0.1 cm. Style color: RHS 143D.
*Ovary.*—Shape: Ovate. Color: RHS 143D.

Fruit and seed set: None observed.
Disease and insect resistance: Somewhat mildew resistant.

COMPARISON WITH PARENTAL AND COMMERCIAL CULTIVARS

'KLENH08448' differs from the proprietary female *Nemesia* plant 'NH05279' (unpatented) in that 'KLENH08448' has medium-sized flowers, while 'NH05279' has small-sized flowers. Additionally, 'KLENH08448' has better and more branching than 'NH05279'.

'KLENH08448' differs from the commercial comparison variety 'KLENH05425' (unpatented) in that 'KLENH08448' is somewhat mildew resistant, while 'KLENH05425' is sensitive to mildew. Additionally, 'KLENH08448' has a more vigorous growth habit than 'KLENH05425'.

I claim:

1. A new and distinct cultivar of *Nemesia* plant named 'KLENH08448' as shown and described herein.

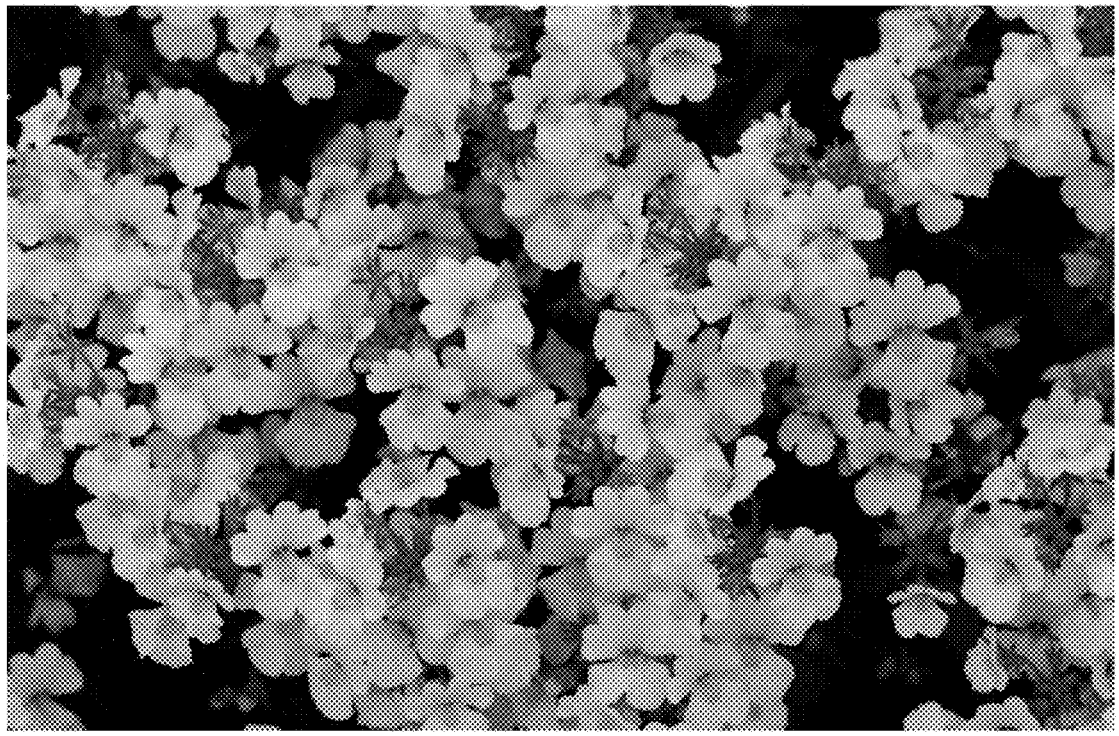

* * * * *